US00PP14042P29

(12) United States Plant Patent
Dümmen

(10) Patent No.: US PP14,042 P2
(45) Date of Patent: Aug. 5, 2003

(54) GERANIUM PLANT NAMED 'DUELIRA'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/228,465

(22) Filed: Aug. 27, 2002

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—C. A. Whealy

(57) ABSTRACT

A new and distinct cultivar of Ivy Geranium plant named 'Duelira', characterized by its upright and outwardly spreading plant habit; freely basal branching habit; freely and early flowering habit; and light red purple-colored double flowers.

1 Drawing Sheet

BOTANICAL CLASSIFICATION/CULTIVAR DENOMINATION

*Pelargonium peltatum* cultivar 'Duelira'.

BACKGROUND OF THE INVENTION

The present invention relates to a new and distinct cultivar of Ivy Geranium plant, botanically known as *Pelargonium peltatum,* and hereinafter referred to by the name 'Duelira'.

The new Ivy Geranium is a product of a planned breeding program conducted by the Inventor in Rheinberg, Germany. The objective of the breeding program was to develop new Ivy Geraniums with attractive flower and foliage colors.

The new Ivy Geranium originated from a cross made by the Inventor in June, 1999 of a proprietary selection of *Pelargonium peltatum* identified as code number F-23-9, not patented, as the female, or seed, parent with a proprietary selection of *Pelargonium peltatum* identified as code number F-02-21, not patented, as the male, or pollen, parent. The cultivar Duelira was discovered and selected by the Inventor as a flowering plant within the progeny from this cross in a controlled environment in Rheinberg, Germany in March, 2001.

Asexual reproduction of the new cultivar by terminal vegetative cuttings taken at Rheinberg, Germany since June, 2001 has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Duelira'. These characteristics in combination distinguish 'Duelira' as a new cultivar and distinguish it from other known Ivy Geranium cultivars:

1. Upright and outwardly spreading plant habit.
2. Freely basal branching habit.
3. Freely and early flowering habit.
4. Light red purple-colored double flowers.

Compared to plants of the female parent, the selection F-23-9, plants of the new Ivy Geranium are more vigorous. Compared to plants of the male parent, the selection F-02-21, plants of the new Ivy Geranium are more compact and differ in flower color.

The new Ivy Geranium can be compared to plants of the cultivar 'Guimongol', disclosed in U.S. Plant Pat. No. 9,352. In side-by-side comparisons conducted in Rheinberg, Germany, plants of the new Ivy Geranium differed from plants of the cultivar Guimongol in the following characteristics:

1. Plants of the new Ivy Geranium were more freely branching than plants of the cultivar Guimongol.
2. Plants of the new Ivy Geranium had larger leaves than plants of the cultivar Guimongol.
3. Plants of the new Ivy Geranium had longer pedicels than plants of the cultivar Guimongol. In addition, pedicels of plants of the new Ivy Geranium were green in color whereas pedicels of plants of the cultivar Guimongol were dark purple in color.
4. Flower color of plants of the new Ivy Geranium was darker red purple than flower color of plants of the cultivar Guimongol.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy Geranium. The photograph comprises a side perspective view of typical flowering plants of 'Duelira' grown in a container.

DETAILED BOTANICAL DESCRIPTION

The cultivar Duelira has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown with three plants per 10.5-cm container. Plants were about eight weeks from unrooted cuttings when the photographs and the detailed botanical description were taken.

In the following description, color references are made to The Royal Horticultural Society Colour Chart, 1995 edition, except where general terms of ordinary dictionary significance are used.

Botanical classification: *Pelargonium peltatum* cultivar Duelira.

Parentage:

*Female parent.*—Proprietary selection of *Pelargonium peltatum* identified as code number F-23-9, not patented.

*Male parent.*—Proprietary selection of *Pelargonium peltatum* identified as code number F-02-21, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About 21 days at 20° C. Winter: About 28 days at 20° C.

*Root description.*—Fine, fibrous; white in color.

*Rooting habit.*—Freely branching.

Plant description:

*General appearance.*—Upright and outwardly spreading plant habit, rounded; densely foliated.

*Growth and branching habit.*—Moderately vigorous. Freely basal branching, about six lateral branches per plant.

*Plant height.*—About 20 cm.

*Plant width.*—About 11 cm.

*Lateral branches.*—Length: About 18 cm. Internode length: About 2.7 cm. Texture: Smooth. Color: 144A.

*Foliage description.*—Arrangement: Alternate, single. Quantity of leaves per lateral branch: About six. Length: About 8.7 cm. Width: About 11.1 cm. Shape: Reniform. Apex: Acute. Base: Peltate. Margin: Crenate. Venation pattern: Palmate. Texture, upper and lower surfaces: Smooth; glabrous. Color: Young and fully expanded foliage, upper surface: 137B. Young and fully expanded foliage, lower surface: 144A. Venation, upper and lower surfaces: 144A. Zonation pattern: Width: About 2 cm. Color: 137A. Petiole: Length: About 5 cm. Diameter: About 2.8 mm. Color, upper and lower surfaces: 144A.

Flower description:

*Flower arrangement.*—Light red purple-colored double flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering; at full flower, plants have about five open and developing umbels with about 15 flowers per umbel.

*Flowering season.*—Flowering continuous spring through summer. Early flowering, plants begin flowering about eight weeks after planting.

*Flower longevity.*—Flowers last about five to seven days on the plant.

*Umbel size.*—Height: About 5.5 cm. Diameter: About 9 cm.

*Flower size.*—Diameter: About 4.5 cm. Depth (height): About 2 cm.

*Flower buds.*—Length: About 1.3 cm. Diameter: About 7 mm. Shape: Ovoid. Color: 144A.

*Petals.*—Quantity per flower: About five. Length: About 2.7 cm. Width: About 1.8 cm. Shape: Obovate. Apex: Rounded. Base: Attenuate. Margin: Entire, sinuate. Texture, upper and lower surfaces: Smooth; glabrous. Color: When opening, upper surface: 58B; venation towards base, 53A. When opening, lower surface: 62A. Fully opened, upper surface: 58C; venation towards base, 53A; color fading towards 58D with subsequent development. Fully opened, lower surface: 62A.

*Petaloids.*—Quantity per flower: About five. Length: About 2 cm. Width: About 1.1 cm. Shape: Obovate. Apex: Rounded. Base: Attenuate. Margin: Entire, sinuate. Texture, upper and lower surfaces: Smooth. Color: When opening, upper surface: 58B; venation towards base, 53A. When opening, lower surface: 62A. Fully opened, upper surface: 58C; venation towards base, 53A; color fading towards 58D with subsequent development. Fully opened, lower surface: 62A.

*Sepals.*—Quantity per flower: About seven, arranged in a single whorl. Length: About 1.3 cm. Width: About 3.1 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 14.7 cm. Diameter: Less than 1 cm. Angle: Erect. Strength: Moderately strong. Texture: Smooth; glabrous. Color: 144A.

*Pedicel* (*individual flower stem*).—Length: About 2.8 cm. Diameter: About 1 mm. Angle: Erect. Strength: Moderately strong. Texture: Pubescent. Color: 144A.

*Reproductive organs.*—Androecium: Anther quantity per flower: About six. Anther length: About 3 mm. Anther shape: Ovate. Anther color: 61B. Pollen amount: Moderate. Pollen color: 28A. Gynoecium: Pistil quantity per flower: One. Pistil length: About 1 cm. Stigma shape: Five-parted, star-shaped. Stigma color: 53A. Style length: About 6 mm. Style color: 2D. Ovary color: 144A.

*Seed/fruit.*—Development of seeds and fruit have not been observed.

Disease/pest resistance: Plants of the new Ivy Geranium have not been observed to be resistant to pathogens and pests common to Ivy Geraniums.

Temperature tolerance: Plants of the new Ivy Geranium have been observed to be tolerant to temperatures ranging from 5 to 40° C.

It is claimed:

1. A new and distinct cultivar of Ivy Geranium plant named 'Duelira', as herein illustrated and described.

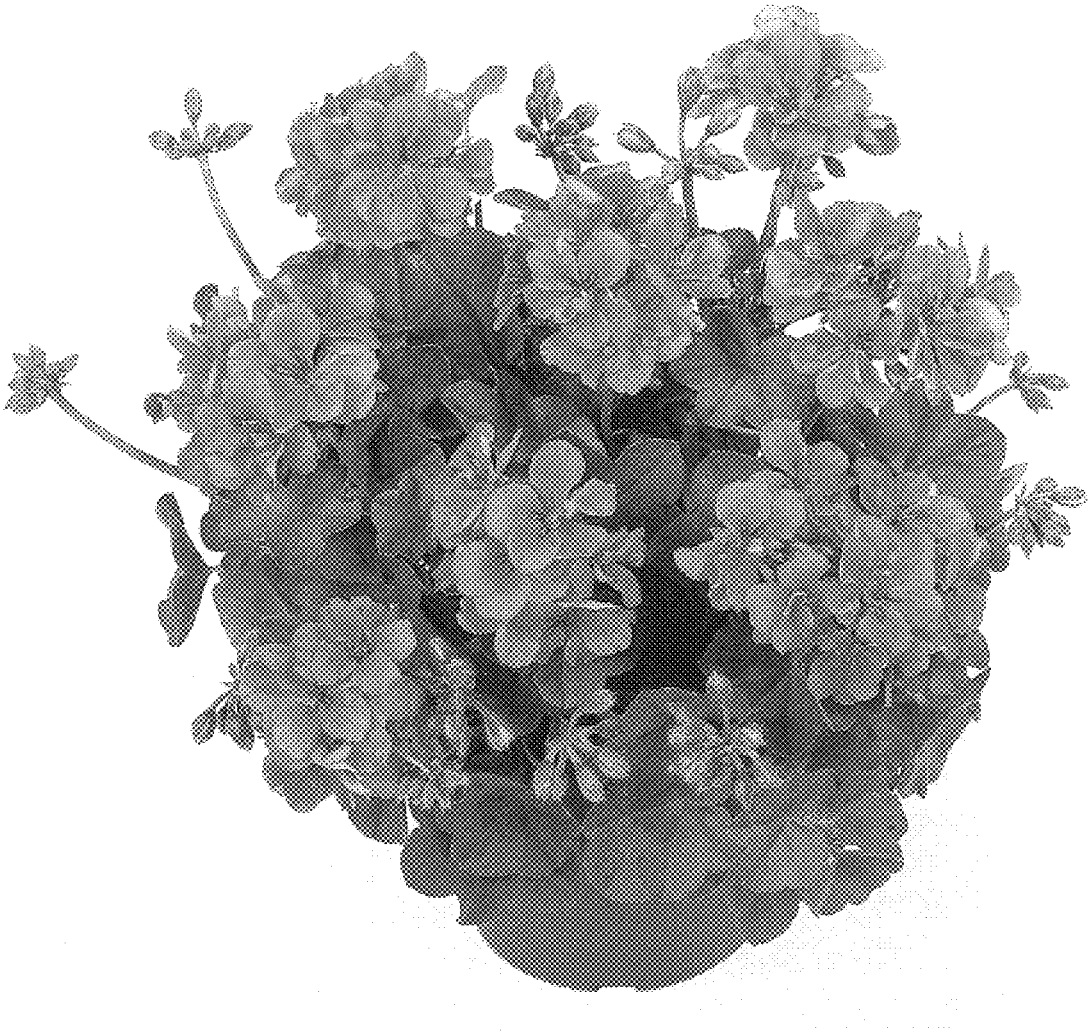

* * * * *